(12) United States Patent
Ginoux

(10) Patent No.: US 11,089,749 B2
(45) Date of Patent: Aug. 17, 2021

(54) MELON VARIETY NUN 16108 MEM

(71) Applicant: NUNHEMS B.V., Nunhem (NL)

(72) Inventor: Jean-Paul Ginoux, Eyragues (FR)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 16/444,266

(22) Filed: Jun. 18, 2019

(65) Prior Publication Data

US 2019/0297817 A1 Oct. 3, 2019

Related U.S. Application Data

(60) Provisional application No. 62/695,437, filed on Jul. 9, 2018.

(51) Int. Cl.
*A01H 6/34* (2018.01)
*A01H 5/10* (2018.01)

(52) U.S. Cl.
CPC ............... *A01H 5/10* (2013.01); *A01H 6/34* (2018.05); *A01H 6/344* (2018.05)

(58) Field of Classification Search
None
See application file for complete search history.

(56) References Cited

U.S. PATENT DOCUMENTS

| 9,185,859 B2 * | 11/2015 | Ginoux .............. C12N 15/8245 |
| 2015/0126380 A1 | 5/2015 | Van Dun |
| 2015/0245570 A1 | 9/2015 | Vogelaar et al. |
| 2017/0071145 A1 | 3/2017 | Tadmor et al. |
| 2017/0240913 A1 | 8/2017 | Schaffer et al. |
| 2017/0335339 A1 | 11/2017 | Van Dun |

OTHER PUBLICATIONS

"Guidelines for the Conduct of Tests for Distinctness, Uniformity and Stability", UPOV, International Union for the protection of new variety of plants, Geneva, UPOV Code: CUCUM_MEL (*Cucumis melo* L.), Apr. 9, 2014, 69 pages.
"Objective Description of Variety Muskmelon/Cantaloupe (*Cucumis melo* L.)", US Department of Agriculture, Agricultural Marketing Service Science and Technology Plant Variety protection office, 2015, 4 pages.
Colijn-Hooymans, et al., "Competence for regeneration of cucumber cotyledons is restricted to specific developmental stages", Plant Cell, Tissue and Organ Culture, vol. 39, Issue 3, Dec. 1994, pp. 211-217.
Hartz, et al., "Cantaloupe Production in California", University of California, Division of Agriculture and Natural Resources, Publication 7218, 2008, pp. 1-4.
Mayberry, et al., "Mixed Melon Production in California", University of California, Division of Agriculture and Natural Resources, Publication 7209, 1996, pp. 1-3.
Needleman, et al., "A general method applicable to the search for similarities in the amino acid sequence of two proteins", Journal of Molecular Biology, vol. 48, Issue 3, Mar. 28, 1970, pp. 443-453.
Nikolova, et al., "Diploidization of cucumber (*Cucumis sativus* L.) haploids by colchicine treatment", Acta Societatis Botanicorum Poloniae, vol. 65, Issue 3-4, 1996, pp. 311-317.
Parvathaneni, et al., "Fingerprinting in cucumber and melon (*Cucumis* spp.) Genotypes using morphological and ISSR markers", Journal of Crop Science and Biotechnology, vol. 14, Issue 1, Mar. 2011, pp. 39-43.
Ren, et al., "Shoot regeneration and ploidy variation in tissue culture of honeydew melon (*Cucumis melo* L. *inodorus*)", In Vitro Cellular & Developmental Biology—Plant, vol. 49, Issue 2, Apr. 2013, pp. 223-229.
Rice, et al., "EMBOSS: The European Molecular Biology Open Software Suite", Trends in Genetics, vol. 16, Issue 6, Jun. 1, 2000, pp. 276-277.
Vidavsky, et al., "Tomato Breeding Lines Resistant and Tolerant to Tomato Yellow Leaf Curl Virus Issued from Lycopersicon hirsutum", Phytopathology, vol. 88, Issue 9, Sep. 1998, pp. 910-914.
Vos, et al., "AFLP: a new technique for DNA fingerprinting", Nucleic Acids Research, vol. 23, Issue 21, Nov. 11, 1995, pp. 4407-4414.
Wijnker, et al., "Hybrid recreation by reverse breeding in *Arabidopsis thaliana*", Nature Protocols, vol. 9, 2014, pp. 761-772.

* cited by examiner

*Primary Examiner* — Brent T Page
(74) *Attorney, Agent, or Firm* — Arent Fox LLP

(57) ABSTRACT

The disclosure provides a new and distinct hybrid melon variety NUN 16108 MEM as well as seeds and plants and fruits thereof. NUN 16108 MEM is a non-sutured cantaloupe melon of the Harper subtype (i.e., having long shelf-life and good taste) with yellow skin and orange flesh, comprising resistance to *Fusarium oxysporum melonis* Race 0 (HR), Race 1 (HR), and Race 2 (HR), *Podosphaera xanthii* Race 1 (IR), Race 2 (IR), and Race 5 (IR), *Golovinomyces cichoracearum* (IR), and *Aphis gossypii*.

22 Claims, 2 Drawing Sheets

MELON VARIETY NUN 16108 MEM

CROSS-REFERENCE TO RELATED APPLICATION

This application claims priority to U.S. Provisional Patent Application No. 62/695,437, filed Jul. 9, 2018, which is hereby incorporated by reference in its entirety.

FIELD OF THE DISCLOSURE

The disclosure relates to the field of plant breeding and, more specifically, to melon variety NUN 16108 MEM. The disclosure further relates to vegetative reproductions of melon variety NUN 16108 MEM, methods for tissue culture of melon variety NUN 16108 MEM and regenerating a plant from such a tissue culture and to phenotypic variants of melon variety NUN 16108 MEM.

BACKGROUND OF THE DISCLOSURE

The goal of plant breeding is to combine various desirable traits in a single variety or hybrid. Such desirable traits may include greater yield, resistance to diseases, insects or other pests, tolerance to heat and drought, better agronomic quality, higher nutritional value, enhanced growth rate, and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype. Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential.

One crop species which has been subject to such breeding programs and is of particular value is the melon. It belongs to the Cucurbitacea family and has originated in Asia. The plant is a large and sprawling annual, grown for its fruit.

The fruit of most species of *Cucumis melo* is often colored attractively, commonly yellow, orange or red. Melon can contain black seeds, which are considered undesirable for some uses. Common types include Persian, Honey Dew, Casaba, Crenshaw, Common/Summer and subtypes such as the popular Galia, Canary, Western Shipper or the new Crispy types. Melon is typically consumed fresh as desserts, snacks, or in salads.

One of the leading consumers of melon is the United States with California as the major producer. Melon is available year-round but supply peaks in August and ends in November.

While breeding efforts to date have provided a number of useful melon varieties with beneficial traits, there remains a great need in the art for new varieties with further improved traits. Such plants would benefit farmers and consumers alike by improving crop yields and/or quality. Breeding objectives include varying the color, size, texture and flavor of the fruit, absence of seeds, optimizing flesh thickness, disease or pest resistance, yield, suitability to various climatic circumstances, solid content (% dry matter), sugar content, and storage properties.

SUMMARY OF VARIOUS ASPECTS OF THE DISCLOSURE

The disclosure provides for melon variety NUN 16108 MEM, products thereof, and methods of using the same. NUN 16108 MEM is a non-sutured cantaloupe melon of the Harper subtype (i.e., having long shelf-life and good taste) with yellow skin and orange flesh, and suitable for the open field.

In one aspect, the disclosure provides a seed of melon variety NUN 16108 MEM, wherein a representative sample of said seed has been deposited under Accession Number NCIMB 43406. The disclosure also provides for a plurality of seeds of melon variety NUN 16108 MEM. The melon seed of variety NUN 16108 MEM may be provided as an essentially homogeneous population of melon seed. The population of seed of melon variety NUN 16108 MEM may be particularly defined as essentially free from other seed. The seed population may be grown into plants to provide an essentially homogeneous population of melon plants as described herein.

The disclosure also provides a plant grown from a seed of melon variety NUN 16108 MEM and a plant part thereof. In another aspect, the disclosure provides for a hybrid melon variety NUN 16108 MEM. The disclosure also provides for a progeny of melon variety NUN 16108 MEM. In another aspect, the disclosure provides a plant or a progeny retaining all or all but one, two or three of the "distinguishing characteristics" or all or all but one, two or three of the "morphological and physiological characteristics" of melon variety NUN 16108 MEM, and methods for producing that plant or progeny.

In one aspect, the disclosure provides a plant or a progeny having all the physiological and morphological characteristics of variety NUN 16108 MEM when grown under the same environmental conditions. In another aspect, the plant or progeny has all or all but one, two or three of the physiological and morphological characteristics of melon variety NUN 16108 MEM when measured under the same environmental conditions and e.g., evaluated at significance levels of 1%, 5% or 10% significance (which can also be expressed as a p-value) for quantitative characteristics, wherein a representative sample of seed of variety NUN 16108 MEM has been deposited under Accession Number NCIMB 43406. In another aspect, the plant or progeny has all or all but one, two or three of the physiological and morphological characteristics as listed in Tables 1 and 2 for variety NUN 16108 MEM when measured under the same environmental conditions and e.g., evaluated at significance levels of 1%, 5% or 10% (which can also be expressed as a p-value) for quantitative characteristics.

In another aspect, the plant of variety NUN 16108 MEM or a progeny thereof has 19, 20, or more or all of the following distinguishing characteristics as shown in Table 3: 1) longer mature blade length; 2) larger mature blade width; 3) shorter petiole length; 4) smaller petiole width; 5) longer peduncle length of young fruit; 6) shorter mature fruit length; 7) larger mature fruit diameter; 8) heavier mature fruit weight 9) smaller blossom scar diameter; 10) larger mature fruit medial; 11) smaller pistil scar; 12) darker greenish yellow color of rind at maturity; 13) pale yellow color of net at edible maturity; 14) darker orange color of flesh near cavity; 15) darker orange color of flesh near center; 16) darker orange color of flesh near rind; 17) higher penetrometer reading; 18) shorter seed cavity length; 19) smaller seed cavity width; and 20) higher number of seeds per fruit, when grown under the same environmental conditions.

In another aspect, the plant of melon variety NUN 16108 MEM, or a part thereof, or a progeny thereof comprises resistance to *Fusarium oxysporum melonis* Race 0 (HR), Race 1 (HR), and Race 2 (HR), *Podosphaera xanthii* Race 1 (IR), Race 2 (IR), and Race 5 (IR), *Golovinomyces cichoracearum* IR, and *Aphis gossypii*, measured according to TG104/5.

In other aspects, the disclosure provides for a plant part obtained from melon variety NUN 16108 MEM, wherein said plant part is: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, a hypocotyl, cotyledon, a scion, a stock, a rootstock, a pistil, an anther, or a flower or a part thereof. Fruits are particularly important plant parts. In another aspect, the plant part obtained from melon variety NUN 16108 MEM is a cell, optionally a cell in a cell or tissue culture. That cell may be grown into a plant of variety NUN 16108 MEM.

The disclosure also provides a cell culture of melon variety NUN 16108 MEM, and a plant regenerated from melon variety NUN 16108 MEM, which plant has all the characteristics of melon variety NUN 16108 MEM, when grown under the same environmental conditions, as well as methods for culturing and regenerating melon variety NUN 16108 MEM. Alternatively, a regenerated plant may have one characteristic that is different from melon variety NUN 16108 MEM.

The disclosure further provides a vegetatively propagated plant of variety NUN 16108 MEM having all or all but one, two or three of the morphological and physiological characteristics of melon variety NUN 16108 MEM, when grown under the same environmental conditions.

The disclosure furthermore provides a melon fruit produced on a plant grown from a seed of melon variety NUN 16108 MEM.

In another aspect, the disclosure provides a seed growing or grown on a plant of variety NUN 16108 MEM (i.e., produced after pollination of the flower of melon variety NUN 16108 MEM).

DEFINITIONS

Figure 1:
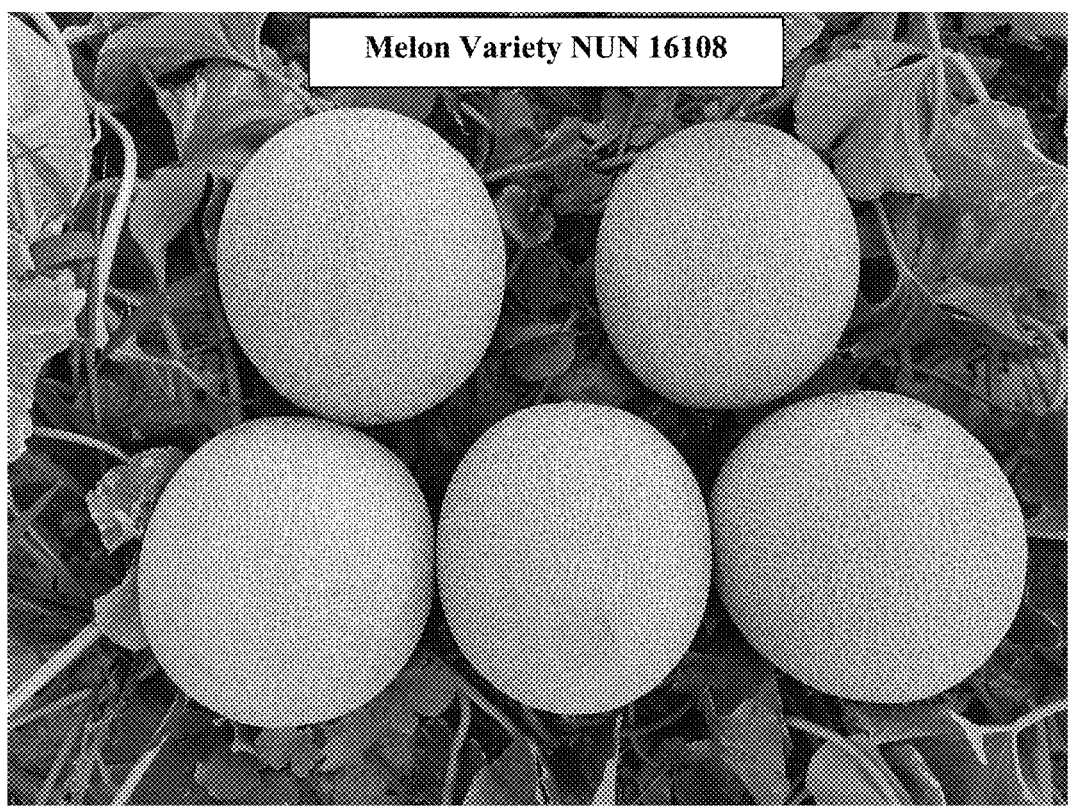
FIG. 1 shows the fruit of melon variety NUN 16108 MEM.
Figure 2:
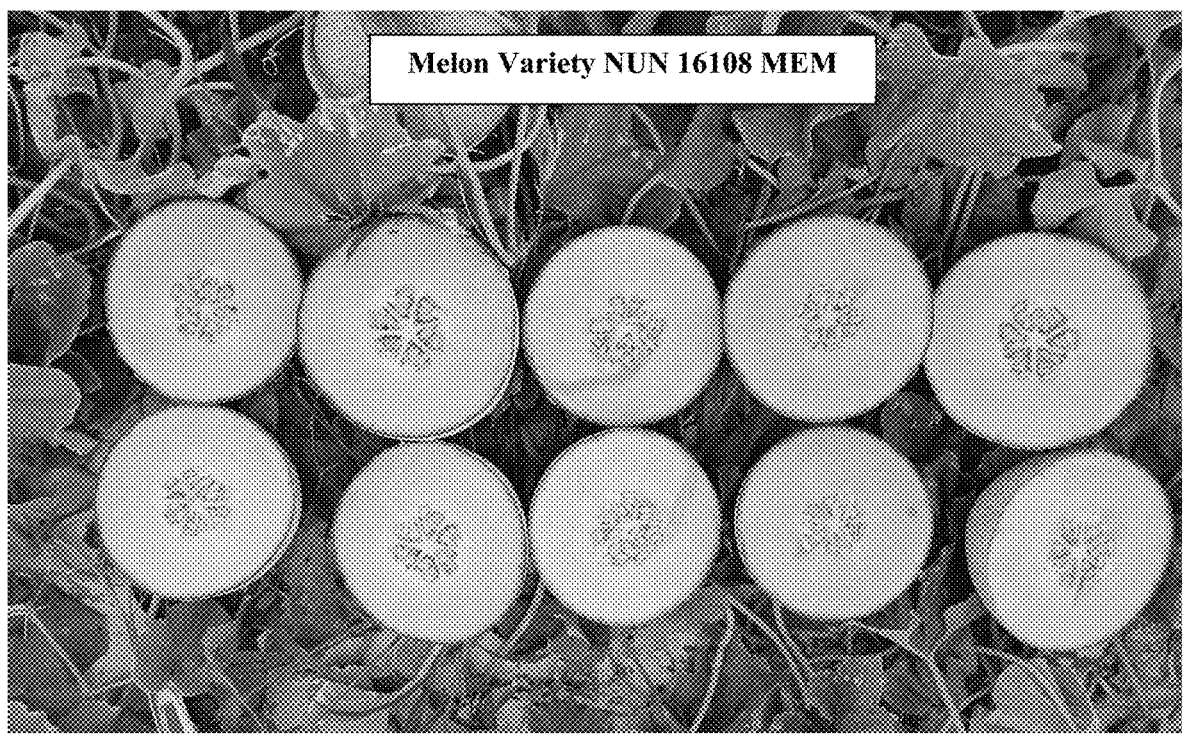
FIG. 2 shows the mature fruit (cross section) of melon variety NUN 16108 MEM.

"Melon" or "muskmelon" refers herein to plants of the species *Cucumis melo*, and fruits thereof. The most commonly eaten part of a melon is the fruit or berry, also known as pepo. The fruit comprises exocarp, mesocarp, endocarp or seed cavity, hypanthium tissue and optionally seed. Exocarp, mesocarp, endocarp or seed cavity, hypanthium tissue, and seed coat of the seed are maternal tissues, so they are genetically identical to the plant on which they grow.

"Cultivated melon" refers to plants of *Cucumis melo* (e.g., varieties, breeding lines or cultivars of the species *C. melo*), cultivated by humans and having good agronomic characteristics.

"Cantaloupe melon" refers to orange-fleshed melons.

The terms "melon plant designated NUN 16108 MEM," "NUN 16108 MEM," "NUN 16108," "NUN 16108 F1," "16108 MEM" or "melon 16108" are used interchangeably herein and refer to a melon plant of variety NUN 16108 MEM, representative seed of which has been deposited under Accession Number NCIMB 43406.

A "seed of NUN 16108 MEM" refers to a melon seed which can be grown into a plant of variety NUN 16108 MEM, wherein a representative sample of viable seed has been deposited under Accession Number NCIMB 43406. A seed can be in any stage of maturity, for example, a mature, viable seed, or an immature, non-viable seed. A seed comprises an embryo and maternal tissues.

An "embryo of NUN 16108 MEM" refers to a "F1 hybrid embryo" as present in a seed of melon variety NUN 16108 MEM, a representative sample of said seed has been deposited under Accession Number NCIMB 43406.

A "seed grown on NUN 16108 MEM" refers to a seed grown on a mature plant of variety NUN 16108 MEM or inside a fruit of melon variety NUN 16108 MEM. The "seed grown on NUN 16108 MEM" contains tissues and DNA of the maternal parent, melon variety NUN 16108 MEM. The "seed grown on NUN 16108 MEM" contains an F1 embryo. When said seed is planted, it grows into a first generation progeny plant of variety NUN 16108 MEM.

A "fruit of NUN 16108 MEM" refers to a fruit containing maternal tissues of melon variety NUN 16108 MEM, as deposited under Accession Number NCIMB 43406. In one option, the fruit contains seed grown on melon variety NUN 16108 MEM. In another option, the fruit does not contain seed, so the fruit is parthenocarpic. The skilled person is familiar with methods for inducing parthenocarpy. Those methods comprise chemically or genetically inducing parthenocarpy. Compounds suitable for chemically inducing parthenocarpy comprise auxins, gibberellins and cytokinins. Methods for genetically inducing parthenocarpy comprise the methods described in US2017/0335339, US2017/0240913, and US2017/0071145. A fruit can be in any stage of maturity, for example, a mature fruit in the yellow stage comprising viable seed, or an immature fruit in the edible green stage comprising non-viable seed.

An "essentially homogeneous population of melon seed" is a population of seeds where at least 97%, 98%, 99% or more of the total population of seed are seeds of melon variety NUN 16108 MEM.

An "essentially homogeneous population of melon plants" is a population of plants where at least 97%, 98%, 99% or more of the total population of plants are plants of melon variety NUN 16108 MEM.

The phrase "essentially free from other seed" refers to a population of seed where less than 3%, 2%, 1% or less of the total population of seed is seed that is not a melon seed or, in another aspect, less than 3%, 2%, 1% or less of the total population of seed is seed that is not seed of melon variety NUN 16108 MEM.

"Tissue culture" or "cell culture" refers to a composition comprising isolated cells of the same or a different type or a collection of such cells organized into parts of a plant. Tissue culture of melon and regeneration of plants therefrom is well known and widely published (see, e.g., Ren et al., In Vitro Cell. Dev. Biol. Plant (2013) 49:223-229; Colijn-Hooymans (1994), Plant Cell, Tissue and Organ Culture 39: 211-217). Similarly, methods of preparing cell cultures are known in the art.

"USDA descriptors" are the plant variety descriptors described for melon in the "Objective description of Variety—Muskmelon/Cantaloupe (*Cucumis melo* L.)", as published by the US Department of Agriculture, Agricultural Marketing Service, Plant Variety Protection Office, Beltsville, Md. 20705 and which can be downloaded from the world-wide web at ams.usda.gov/under services/plant-variety-protection/pvpo-c-forms under muskmelon. "Non-USDA descriptors" are other descriptors suitable for describing melon.

"UPOV descriptors" are the plant variety descriptors described for melon in the "Guidelines for the Conduct of Tests for Distinctness, Uniformity and Stability, TG/104/5 (Geneva 2006, as last updated in 2014-04-09), as published by UPOV (International Union for the Protection of New Varieties and Plants) and which can be downloaded from the world-wide web at upov.int/edocs/tgdocs/en/tg104.pdf and is herein incorporated by reference in its entirety. Likewise, "UPOV methods" to determine specific parameters for the characterization of melon are described at upov.int.

"RHS" or "RHS color chart" refers to the color chart of the Royal Horticultural Society (UK), which publishes a botanical color chart quantitatively identifying colors by a defined numbering system. The chart may be purchased from Royal Horticulture Society Enterprise Ltd. RHS Garden; Wisley, Woking; Surrey GU236QB, UK, e.g., the RHS color chart 2007.

"Plant part" includes any part of a plant, such as a plant organ (e.g., harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, hypocotyl, cotyledon, a scion, a graft, a stock, a rootstock, a pistil, an anther, and a flower or parts of any of these and the like. Seed can be mature or immature. Pollen or ovules may be viable or non-viable. Also, any developmental stage is included, such as seedlings, cuttings prior or after rooting, mature plants or leaves. Alternatively, a plant part may also include a plant seed which comprises maternal tissues of melon variety NUN 16108 MEM and an embryo having one or two sets of chromosomes derived from the parent plant, e.g., from melon variety NUN 16108 MEM. Such an embryo comprises two sets of chromosomes derived from melon variety NUN 16108 MEM, if it is produced from self-pollination of said variety, while an embryo derived from cross-fertilization of melon variety NUN 16108 MEM, will comprise only one set of chromosomes from said variety.

"Reference Variety for NUN 16108 MEM" refers herein to variety NUN 26191 MEM, which has been planted in a trial together with melon variety NUN 16108 MEM. The characteristics of melon variety NUN 16108 MEM were compared to the characteristics of the Reference Variety as shown in Tables 1 and 2. The distinguishing characteristics between melon variety NUN 16108 MEM and the Reference Variety are shown in Table 3.

"Rootstock" or "stock" refers to the plant selected for its root system, in particular for the resistance of the roots to diseases or stress (e.g., heat, cold, salinity etc.). Generally, the quality of the fruit of the plant providing the rootstock is less important.

"Scion" refers to a part of the plant attached to the rootstock. This plant is selected for its stems, leaves, flowers, or fruits. The scion contains the desired genes to be duplicated in future production by the stock/scion plant and may produce the desired melon fruit.

"Stock/scion" or "grafted plant" refers to a melon plant comprising a rootstock from one plant grafted to a scion from another plant.

"Harvest maturity" is referred to as the stage at which a melon fruit is ripe or ready for harvest or the optimal time to harvest the fruit for the market, for processing or for consumption. In one aspect, harvest maturity is the stage which allows proper completion of the normal ripening.

"Flavor" refers to the sensory impression of a food or other substance, especially a melon fruit or fruit part (fruit flesh) and is determined mainly by the chemical senses of taste and smell. Flavor is influenced by texture properties and by volatile and/or non-volatile chemical components (organic acids, lipids, carbohydrates, salts etc.).

"Aroma" refers to smell (or odor) characteristics of melon fruits or fruit parts (fruit flesh).

"Harvested plant material" refers herein to plant parts (e.g., fruits detached from the whole plant), which have been collected for further storage and/or further use.

"Yield" means the total weight of all melon fruits harvested per hectare of a particular line or variety. It is understood that "yield" expressed as weight of all melon fruits harvested per hectare can be obtained by multiplying the number of plants per hectare times the "yield per plant".

"Marketable yield" means the total weight of all marketable melon fruits, especially fruit which is not cracked, damaged or diseased, harvested per hectare of a particular line or variety. A "marketable fruit" is a fruit that has commercial value.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progeny plant, the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Tables 1 and 2 or "all or all but one, two or three of the physiological and morphological characteristics" of Tables 1 and 2.

The physiological and/or morphological characteristics mentioned above are commonly evaluated at significance levels of 1%, 5% or 10% if they are numerical (quantitative), or for having an identical degree (or type) if not numerical (not quantitative), if measured under the same environmental conditions. For example, a progeny plant or a Single Locus Converted plant or a mutated plant of variety NUN 16108 MEM, may have one or more (or all) of the essential physiological and/or morphological characteristics of said variety listed in Tables 1 and 2, as determined at the 5% significance level (i.e., $p<0.05$), when grown under the same environmental conditions.

"Distinguishing characteristics" or "distinguishing morphological and/or physiological characteristics" refers herein to the characteristics which distinguish the new variety from other melon varieties, such as the Reference Variety (i.e., are different), when grown under the same environmental conditions. The distinguishing characteristics between melon variety NUN 16108 MEM and its Reference Variety are described herein and can be seen in Table 3. When comparing melon variety NUN 16108 MEM to other varieties, the distinguishing characteristics may be different. In one aspect, the distinguishing characteristics may therefore include one, two, three or more (or all) of the characteristics listed in Tables 1 and 2. All numerical distinguishing characteristics are statistically significantly different at $p<0.05$ between melon variety NUN 16108 MEM and the other variety (e.g., the Reference Variety).

Melon variety NUN 16108 MEM has the following distinguishing characteristics when compared to the Reference Variety as shown in Table 3: 1) longer mature blade length; 2) larger mature blade width; 3) shorter petiole length; 4) smaller petiole width; 5) longer peduncle length of young fruit 6) shorter mature fruit length; 7) larger mature fruit diameter; 8) heavier mature fruit weight; 9) smaller blossom scar diameter; 10) larger mature fruit medial; 11) smaller pistil scar; 12) darker greenish yellow color of rind at maturity; 13) pale yellow color of net at edible maturity; 14) darker orange color of flesh near cavity; 15) darker orange color of flesh near center; 16) darker orange color of flesh near rind; 17) higher penetrometer reading; 18) shorter seed cavity length; 19) smaller seed cavity width; and 20) higher number of seeds per fruit, when grown under the same environmental conditions.

Thus, a melon plant "comprising the distinguishing characteristics of melon variety NUN 16108 MEM" (such as a progeny plant) refers herein to a plant which does not differ significantly from said variety in the distinguishing characteristics above. Therefore, in one aspect, the disclosure provides a plant which does not differ significantly from melon variety NUN 16108 MEM in the distinguishing characteristics above.

Similarity and differences between two different plant lines or varieties can be determined by comparing the number of morphological and/or physiological characteristics that are the same (i.e., statistically not significantly different) or that are different (i.e., statistically significantly different) between the two plant lines or varieties using plants grown under the same environmental conditions. A numerical characteristic is considered to be "the same" when the value for a numeric characteristic is not significantly different at the 1% ($p<0.01$) or 5% ($p<0.05$) significance level, using one way analysis of variance (ANOVA), a standard method known to the skilled person. Non-numerical or "degree" or "type" characteristic is considered "the same" when the values have the same "degree" or "type" when scored using USDA and/or UPOV descriptors, if the plants are grown under the same environmental conditions.

A "plant line" is, for example, a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation," "vegetative reproduction," or "clonal propagation" are used interchangeably herein and mean a method of taking a plant part and inducing or allowing that plant part to form at least roots, and also refer to the plant or plantlet obtained by that method. Optionally, the vegetative propagation is grown into a mature plant. The skilled person is aware of what plant parts are suitable for use in the method.

"Crossing" refers to the mating of two parent plants. The term encompasses "cross-pollination" and "selfing".

"Selfing" refers to self-pollination of a plant, i.e., the transfer of pollen from the anther to the stigma of the same plant.

"Cross-pollination" refers to the fertilization by the union of two gametes from different plants.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

The term "traditional breeding techniques" encompasses herein crossing, selfing, selection, doubled haploid production, embryo rescue, protoplast fusion, marker assisted selection, mutation breeding etc. as known to the breeder (i.e., methods other than genetic modification/transformation/transgenic methods), by which, for example, a genetically heritable trait can be transferred from one melon line or variety to another.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 16108 MEM. A progeny may be obtained by regeneration of cell culture or tissue culture or parts of a plant of said variety or selfing of a plant of said variety or by producing seeds of a plant of said variety. In further aspects, progeny may also encompass plants obtained from crossing of at least one plant of said variety with another melon plant of the same variety or another variety or line, or with wild melon plants. A progeny may comprise a mutation or a transgene. A "first generation progeny" is the progeny directly derived from, obtained from, obtainable from or derivable from the parent plant by, e.g., traditional breeding methods (selfing and/or cross-pollinating) or regeneration (optionally combined with transformation or mutation). Thus, a plant of variety NUN 16108 MEM is the male parent, the female parent or both of a first generation progeny of melon variety NUN 16108 MEM. Progeny may have all the physiological and morphological characteristics of melon variety NUN 16108 MEM, when grown under the same environmental conditions. Using methods such as backcrossing, recurrent selection, mutation or transformation, one or more specific characteristics may be introduced into said variety, to provide or a plant comprising all but 1, 2, or 3 of the morphological and physiological characteristics of melon variety NUN 16108 MEM.

The terms "gene converted" or "conversion plant" or "single locus converted plant" in this context refer to melon plants which are developed by traditional breeding techniques, e.g., backcrossing, or via genetic engineering or through mutation breeding, wherein essentially all of the desired morphological and physiological characteristics of the parent variety or line are recovered, in addition to the one or more characteristics introduced into the parent via e.g., the backcrossing technique (optionally including reverse breeding or reverse synthesis of breeding lines). It is understood that not only the addition of a further characteristic (e.g., addition of gene conferring a further characteristic, such as a disease resistance gene), but also the replacement/modification of an existing characteristic by a different characteristic is encompassed herein (e.g., mutant allele of a gene can modify the phenotype of a characteristic).

Likewise, a "Single Locus Converted (Conversion) Plant" refers to plants developed by plant breeding techniques comprising or consisting of mutation breeding and/or by genetic transformation and/or by traditional breeding techniques, such as backcrossing, wherein essentially all of the desired morphological and physiological characteristics of a melon variety are recovered in addition to the characteristics of the single locus having been transferred into the—variety via above-mentioned technique, or wherein the morphological and physiological characteristic of the variety has been replaced/modified in the variety. In case of a hybrid, the gene may be introduced, or modified, in the male or female parental line.

"Average" refers herein to the arithmetic mean.

The term "mean" refers to the arithmetic mean of several measurements. The skilled person understands that the appearance of a plant depends to some extent on the growing conditions of said plant. Thus, the skilled person understands suitable growing conditions for melon variety NUN 16108 MEM. The mean, if not indicated otherwise within this application, refers to the arithmetic mean of measurements on at least 10 different, randomly selected plants of a variety or line.

DETAILED DESCRIPTION OF VARIOUS ASPECTS OF THE DISCLOSURE

The disclosure relates to a plant of variety NUN 16108 MEM, wherein a representative sample of seeds of said variety has been deposited under the Budapest Treaty, with Accession number NCIMB 43406. NUN 16108 MEM is a non-sutured cantaloupe melon of the Harper subtype (i.e., having long shelf-life and good taste) with yellow skin and orange flesh, and suitable for the open field.

The disclosure also relates to a seed of melon variety NUN 16108 MEM, wherein a representative sample of said seed has been deposited under the Budapest Treaty, with Accession number NCIMB 43406.

In another aspect, the disclosure provides for a plant part of variety NUN 16108 MEM, such as a fruit, a representative sample of seed from said variety has been deposited under the Budapest Treaty, with Accession number NCIMB 43406.

In another aspect, a seed of hybrid variety NUN 16108 MEM is obtainable by crossing the male parent of melon variety NUN 16108 MEM with the female parent of melon variety NUN 16108 MEM and harvesting the seeds produced on the female parent. The resultant seeds of said variety can be grown to produce plants of said variety. In one aspect, a seed or a plurality of seeds of said variety are packaged into a container of any size or type (e.g., bags, cartons, cans, etc.). The seed may be disinfected, primed and/or treated with various compounds, such as seed coatings or crop protection compounds. The seed produces a plant of variety NUN 16108 MEM.

Also provided is a plant of melon variety NUN 16108 MEM, or a fruit or other plant part thereof, produced from a seed, wherein a representative sample of said seeds has been deposited under the Budapest Treaty, with Accession Number NCIMB 43406.

Also provided is a plant part obtained from variety NUN 16108 MEM, wherein said plant part is a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, a hypocotyl, cotyledon, a scion, a stock, a rootstock, a pistil, an anther, and a flower or a part thereof. Fruits are particularly important plant parts. Fruits may be parthenocarpic, or seedless, or contain immature or nonviable seeds, or contain viable seeds. In a further aspect, the plant part obtained from melon variety NUN 16108 MEM, is a cell, optionally a cell in a cell or tissue culture. That cell may be grown into a plant of variety NUN 16108 MEM. A part of melon variety NUN 16108 MEM (or of a progeny of that variety or of a plant having all physiological and/or morphological characteristics but one, two or three of melon variety NUN 16108 MEM) further encompasses any cells, tissues, organs obtainable from the seedlings or plants in any stage of maturity.

The disclosure also provides for a food or feed product or a processed product comprising or consisting of a plant part described herein. Preferably, the plant part is a melon fruit or part thereof and/or an extract from a fruit or another plant part described herein comprising at least one cell of melon variety NUN 16108 MEM. The food or feed product may be fresh or processed, e.g., dried, grinded, powdered, pickled, chopped, cooked, roasted, in a sauce, in a sandwich, pasted, puréed or concentrated, juiced, sliced, canned, steamed, boiled, fried, blanched or frozen, etc.

Such a plant part of melon variety NUN 16108 MEM can be stored and/or processed further. The disclosure thus also provides for a food or feed product comprising one or more of such parts, such as canned, chopped, cooked, roasted, in a sauce, in a sandwich, pasted, puréed or concentrated, juiced, frozen, dried, pickled, or powdered melon fruit from melon variety NUN 16108 MEM or from progeny of said variety, or from a derived variety, such as a plant having all but one, two or three physiological and/or morphological characteristics of melon variety NUN 16108 MEM.

In another aspect, the disclosure provides for a melon fruit of variety NUN 16108 MEM, or part of a fruit of said variety. The fruit can be in any stage of maturity, for example, immature or mature. In another embodiment, the disclosure provides for a container comprising or consisting of a plurality of harvested melon fruits or parts of fruits of said variety, or fruits of progeny thereof, or fruits of a derived variety.

Marketable fruits are generally sorted by size and quality after harvest. Alternatively, the fruits can be sorted by expected shelf life, pH or Brix.

In another aspect, the plant, plant part or seed of melon variety NUN 16108 MEM is inside one or more containers. For example, the disclosure provides containers such as cans, boxes, crates, bags, cartons, Modified Atmosphere Packaging, films (e.g., biodegradable films), etc. comprising a plant or part of a plant (fresh and/or processed) or a seed of melon variety NUN 16108 MEM. In a particular aspect, the container comprises a plurality of seeds of melon variety NUN 16108 MEM, or a plurality of plant parts of melon variety NUN 16108 MEM.

The disclosure further relates to a melon variety NUN 16108 MEM, which when compared to its Reference Variety has the following distinguishing characteristics as shown in Table 3: 1) longer mature blade length; 2) larger mature blade width; 3) shorter petiole length; 4) smaller petiole width; 5) longer peduncle length of young fruit; 6) shorter mature fruit length; 7) larger mature fruit diameter; 8) heavier mature fruit weight 9) smaller blossom scar diameter; 10) larger mature fruit medial; 11) smaller pistil scar; 12) darker greenish yellow color of rind at maturity; 13) pale yellow color of net at edible maturity; 14) darker orange color of flesh near cavity; 15) darker orange color of flesh near center; 16) darker orange color of flesh near rind; 17) higher penetrometer reading; 18) shorter seed cavity length; 19) smaller seed cavity width; and 20) higher number of seeds per fruit, where the characteristics are determined at the 5% significance level for plants grown under the same environmental conditions. Also encompassed are parts of that plant.

In one aspect, a plant of variety NUN 16108 MEM or a progeny plant thereof, comprises all of the morphological and/or physiological characteristics (i.e., average values of characteristics, as indicated on the USDA Objective description of variety—melon (unless indicated otherwise)) as shown in Tables 1 and 2, where the characteristics are determined at the 5% significance level for plants grown under the same environmental conditions. A part of this plant is also provided.

In another aspect, NUN 16108 MEM comprises resistance to *Fusarium oxysporum melonis* Race 0 (HR), Race 1 (HR), and Race 2 (HR), *Podosphaera xanthii* Race 1 (IR), Race 2 (IR), and Race 5 (IR), *Golovinomyces cichoracearum* IR, and *Aphis gossypii*, measured according to UPOV standards described in TG/104/5.

The disclosure further provides a melon plant which does not differ from the physiological and morphological characteristics of the plant of variety NUN 16108 MEM as determined at the 1%, 2%, 3%, 4% or 5% significance level when grown under the same environmental conditions. In a particular aspect, the plants are measured in the same trial (e.g., the trial is conducted as recommended by the USDA or UPOV). The disclosure also comprises a part of said plant, preferably a fruit or part thereof.

The disclosure also provides a tissue or cell culture comprising cells of melon variety NUN 16108 MEM. Such a tissue culture can, for example, be grown on plates or in liquid culture, or be frozen for long term storage. The cells of melon variety NUN 16108 MEM used to start the culture can be selected from any plant part suitable for vegetative reproduction, or in a particular aspect can be cells of an embryo, meristem, a cotyledon, a hypocotyl, pollen, a leaf, an anther, a root, a root tip, a pistil, a petiole, a flower, a fruit, seed or a stem. In another particular aspect, the tissue culture does not contain somaclonal variation or has reduced somaclonal variation. The skilled person is familiar with methods to reduce or prevent somaclonal variation, including regular reinitiation.

In one aspect, the disclosure provides a melon plant regenerated from the tissue or cell culture of melon variety NUN 16108 MEM, wherein the regenerated plant is not significantly different from melon variety NUN 16108 MEM, in all, or all but one, two or three, of the physiological and morphological characteristics (e.g., determined at the 5% significance level when grown under the same environmental conditions). Optionally, the plant has one, two or three of the physiological and morphological characteristics that are affected by a mutation or by transformation. In another aspect, the disclosure provides a melon plant regenerated from the tissue or cell culture of melon variety NUN 16108 MEM, wherein the plant has all of the physiological and morphological characteristics of said variety determined (e.g., at the 5% significance level) when grown under the same environmental conditions. Similarity or difference of a characteristic is determined by measuring that characteristics on a representative number of plants grown under the same environmental conditions, determining whether type/degree characteristics are the same and determining whether numerical characteristics are different at the 5% significance level.

Melon variety NUN 16108 MEM or its progeny, or a plant having all physiological and/or morphological characteristics but one, two or three which are different from those of melon variety NUN 16108 MEM, can also be reproduced using vegetative reproduction methods. Therefore, the disclosure provides for a method of producing a plant, or a plant part, of melon variety NUN 16108 MEM, comprising vegetative propagation of said variety. Vegetative propagation comprises regenerating a whole plant from a plant part of NUN 16108 MEM or from a progeny or from or a plant having all physiological and/or morphological characteristics of said variety but one, two or three different characteristics, such as a cutting, a cell culture or a tissue culture.

The disclosure also provides methods of vegetatively propagating a part of the plant of the variety NUN 16108 MEM. In certain aspects, the method comprises: (a) cultivating tissue or cells capable of being propagated from melon variety NUN 16108 MEM, to obtain proliferated shoots; and (b) rooting said proliferated shoots, to obtain rooted plantlets. Steps (a) and (b) may also be reversed, i.e., first cultivating said tissue to obtain roots and then cultivating the tissue to obtain shoots, thereby obtaining rooted plantlets. The rooted plantlets may then be further grown, to obtain plants. In one embodiment, the method further comprises step (c) growing plants from said rooted plantlets. Therefore, the method also comprises regenerating a whole plant from a part of the plant of variety NUN 16108 MEM. In a particular aspect, the part of the plant to be propagated is a cutting, a cell culture or a tissue culture.

The disclosure also provides for a vegetatively propagated plant of variety NUN 16108 MEM, (or from progeny of melon variety NUN 16108 MEM or from a plant having all but one, two or three physiological and/or morphological characteristics of melon variety NUN 16108 MEM), wherein the plant has all of the morphological and physiological characteristics of melon variety NUN 16108 MEM, when the characteristics are determined (e.g., at the 5% significance level) for plants grown under the same conditions. In another aspect, the propagated plant has all but one, two or three of the morphological and physiological characteristics of melon variety NUN 16108 MEM, when the characteristics are determined (e.g., at the 5% significance level) for plants grown under the same conditions. A part of said propagated plant or said propagated plant with one, two or three differences is also provided.

In another aspect, the disclosure provides a method for producing a melon plant part, such as a fruit, comprising growing a plant of variety NUN 16108 MEM until it sets at least one fruit, and collecting the fruit. Preferably, the fruit is collected at harvest maturity. In another aspect, the fruit is collected when the seed is ripe. In a particular aspect, all fruits on a truss can be harvested together. In another particular aspect, all fruit on a melon plant can be harvested at the same time. A plant of variety NUN 16108 MEM can be produced by seeding directly in the soil (e.g., the field) or by germinating the seeds in a controlled environment (e.g., greenhouses) and optionally then transplanting the seedlings into the field (see, e.g., https://anrcatalog.ucanr.edu/pdf/7209.pdf). For example, a seed is sown into a prepared seed bed in a field where the plant remains for its entire life. Alternatively, the melon seed may be planted through a black plastic mulch. The dark plastic will absorb heat from the sun, warming the soil early. It will also help to conserve moisture during the growing season, controls weeds, and makes harvesting easier and cleaner (see, e.g., https://anrcatalog.ucanr.edu/pdf/7218.pdf). Melon can also be grown entirely in greenhouses.

In still another aspect, the disclosure provides a method of producing a melon plant, comprising crossing a plant of variety NUN 16108 MEM with a second melon plant at least once, allowing seed to develop and optionally harvesting said progeny seed. The skilled person can select progeny from said crossing. Optionally, the progeny (grown from the progeny seed) is crossed twice, thrice, or four, five, six or seven times, and allowed to set seed. In one aspect, the first "crossing" further comprises planting seeds of a first and a second parent melon plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

In yet another aspect, the disclosure provides a method of producing a plant, comprising selfing melon variety NUN 16108 MEM one or more times, and selecting a progeny plant from said selfing. In one aspect, the progeny plant retains all or all but one, two or three of the physiological and morphological characteristics of melon variety NUN 16108 MEM, when grown under the same environmental conditions. In a different aspect, the progeny plant comprises all of the physiological and morphological characteristic of melon variety NUN 16108 MEM of Tables 1 and 2.

In other aspects, the disclosure provides a progeny plant of variety NUN 16108 MEM, such as a progeny plant obtained by further breeding with said variety. Further breeding with melon variety NUN 16108 MEM includes selfing that variety and/or cross-pollinating said variety with another melon plant one or more times. In a particular aspect, the disclosure provides for a progeny plant that retains all, or all but one, two or three, of the morphological and physiological characteristics of melon variety NUN 16108 MEM, optionally all or all but one, two or three of the characteristics as listed in Tables 1 and 2, determined at the 5% significance level for numerical characteristics, when grown under the same environmental conditions. In an aspect, the progeny is a first generation progeny, i.e., the ovule or the pollen (or both) used in the crossing is an ovule or pollen of melon variety NUN 16108 MEM, where the pollen comes from an anther of melon variety NUN 16108 MEM and the ovule comes from an ovary of melon variety NUN 16108 MEM. In another aspect, the disclosure provides for a vegetative reproduction of melon variety NUN 16108 MEM, and a plant having all, or all but 1, 2, or 3 of the physiological and morphological characteristics of melon variety NUN 16108 MEM (e.g., as listed in Tables 1 and 2).

The disclosure also provides a method for collecting pollen of melon variety NUN 16108 MEM, comprising collecting pollen from a plant of variety NUN 16108 MEM. Alternatively, the method comprises growing plant of variety NUN 16108 MEM until at least one flower of said variety contains pollen and collecting the pollen. In a particular aspect, the pollen is collected when it is mature or ripe. A suitable method for collecting pollen comprises collecting anthers or the part of the anther that contains pollen, for example, by cutting the anther or the part of the anther off. Pollen can be collected in a container. Optionally, collected pollen can be used to pollinate a melon flower.

The morphological and/or physiological differences between two different individual plants described herein (e.g., between melon variety NUN 16108 MEM and a progeny of said variety) or between a plant of variety NUN 16108 MEM, or progeny of said variety, or a plant having all, or all but 1, 2, or 3, of the physiological and morphological characteristics of melon variety NUN 16108 MEM, and another known variety can easily be established by growing said variety under the same environmental conditions (in the same field, optionally next to each other), preferably repeated in several locations which are suitable for cultivation of melons, and measuring the morphological and physiological characteristics of a representative number of plants (e.g., to calculate an average value and to determine the variation range/uniformity within the variety). For example, trials can be carried out in Acampo Calif., USA (N 38 degrees 07'261"/W 121 degrees 18' 807", USA), whereby various characteristics, for example, maturity, days from seeding to harvest, plant habit, plant attitude, leaf shape, leaf color, blistering, numbers of flowers per leaf axil, number of calyx lobes, number of petals, fruit group, immature fruit color, mature fruit color, pungency, flavor, fruit glossiness, fruit size, fruit shape, average number of fruits per plant, seed size, seed weight, anthocyanin level, disease resistance, insect resistance, can be measured and directly compared for species of melon. Thus, the disclosure comprises a melon plant having one, two or three physiological and/or morphological characteristics which are different from those of the plant of variety NUN 16108 MEM, and which otherwise has all the physiological and morphological characteristics of said variety, when determined (e.g., at the 5% significance level for quantitative characteristics or determined by type for non-quantitative characteristics) for plants grown under the same environmental conditions. In another aspect, the different characteristic is affected by a mutation, optionally induced mutation, or by transformation.

The morphological and physiological characteristics of melon variety NUN 16108 MEM are provided, for example, in Tables 1 and 2, as collected in a trial according to USDA and/or UPOV standards. Encompassed herein is also a plant obtainable from melon variety NUN 16108 MEM, (e.g., by selfing and/or crossing and/or backcrossing with said variety and/or progeny of said variety) comprising all or all but one, two or three of the physiological and morphological characteristics of melon variety NUN 16108 MEM listed in Tables 1 and 2 (as determined at the 5% significance level for numerical characteristics or identical for non-numerical characteristics) when grown under the same environmental conditions and/or comprising one or more (or all; or all except one, two or three) characteristics when grown under the same environmental conditions. The morphological and/or physiological characteristics may vary somewhat with variation in the environment (e.g., temperature, light intensity, day length, humidity, soil, fertilizer use, disease vectors), which is why a comparison under the same environmental conditions is preferred. Colors can best be measured using the Royal Horticultural Society (RHS) Chart.

Also, at-harvest and/or post-harvest characteristics of fruits can be compared, such as cold storage holding quality, post-harvest flesh firmness, and Brix can be measured using known methods. (Fruit) Flesh firmness can, for example, be measured using a penetrometer, e.g., by inserting a probe into the fruit flesh and determining the insertion force, or by other methods. Fruit flesh firmness can for example be measured using a "FT 327 Penetrometer", available from QA Supplies LLC, 1185 Pineridge Road, Norfolk, Va. 23502.

The disclosure provides for methods of producing a plant which retain all the morphological and physiological characteristics of a plant described herein. The disclosure also provides for methods of producing a plant comprising all but 1, 2, 3 or more of the morphological and physiological characteristics of melon variety NUN 16108 MEM (e.g., as listed in Tables 1 and 2), but which are still genetically closely related to said variety. The relatedness can, for example, be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to melon variety NUN 16108 MEM, if its DNA fingerprint is at least 80%, 90%, 95% or 98% identical to the fingerprint of melon variety NUN 16108 MEM. In a particular aspect, AFLP markers are used for DNA fingerprinting (see, e.g., Vos et al. 1995, Nucleic Acid Research 23: 4407-4414). A closely related plant may have a Jaccard's Similarity index of at least about 0.8, preferably at least about 0.9, 0.95, 0.98 or more (see, e.g., Parvathaneni et al., J. Crop Sci. Biotech. 2011 (March) 14 (1): 39-43). The disclosure also provides a plant obtained or selected by applying these methods on melon variety NUN 16108 MEM. Such a plant may be produced by traditional breeding techniques, or mutation or transformation or in another aspect, a plant may simply be identified and selected amongst plants of said variety, or progeny of said variety, e.g., by identifying a variant of melon variety NUN 16108 MEM, which variant differs from the variety described herein in one, two or three of the morphological and/or physiological characteristics (e.g., characteristics listed in Tables 1 and 2). In one aspect, the disclosure provides a plant of variety NUN 16108 MEM, having a Jaccard's Similarity index with said variety of at least 0.8, e.g., at least 0.85, 0.9, 0.95, 0.98 or even at least 0.99.

In some aspects, the disclosure provides a melon plant comprising genomic DNA having at least 95%, 96%, 97%, 98% or 99% sequence identity compared to the genomic DNA sequence of a plant of variety NUN 16108 MEM as to be deposited under Accession Number NCIMB 43406. In some aspects, the melon plant further comprises all or all but 1, 2, or 3 of the morphological and physiological characteristics of melon variety NUN 16108 MEM (e.g., as listed in Tables 1 and 2). In other aspects, the melon plant is a hybrid derived from a seed or plant of variety NUN 16108 MEM.

For the purpose of this disclosure, the "sequence identity" of nucleotide sequences, expressed as a percentage, refers to the number of positions in the two optimally aligned sequences which have identical residues (×100) divided by the number of positions compared. A gap, i.e., a position in the pairwise alignment where a residue is present in one sequence but not in the other, is regarded as a position with non-identical residues. A pairwise global sequence alignment of two nucleotide sequences is found by aligning the two sequences over the entire length according to the Needleman and Wunsch global alignment algorithm described in Needleman and Wunsch, 1970, J. Mol. Biol. 48(3):443-53). A full implementation of the Needleman-Wunsch global alignment algorithm is found in the needle program in The European Molecular Biology Open Software Suite (see, e.g., EMBOSS, Rice et al., Trends in Genetics June 2000, vol. 16, No. 6. pp. 276-277).

The disclosure also provides methods for determining the identity of parental lines of plants described herein, in particular the identity of the female line. US2015/0126380, which is hereby incorporated by reference, relates to a non-destructive method for analyzing maternal DNA of a seed. In this method, the DNA is dislodged from the seed coat surface and can be used to collect information on the genome of the maternal parent of the seed. This method for analyzing maternal DNA of a seed comprises contacting a seed with a fluid to dislodge DNA from the seed coat surface, and analyzing the DNA thus dislodged from the seed coat surface using methods known in the art. The skilled person is thus able to determine whether a seed has grown on a plant of a plant of variety NUN 16108 MEM, or is a progeny of said variety, because the seed coat of the seed is a maternal tissue genetically identical to melon variety NUN 16108 MEM. In one aspect, the disclosure relates to a maternal tissue of melon variety NUN 16108 MEM. In another aspect, the disclosure relates to a melon seed comprising a maternal tissue of melon variety NUN 16108 MEM. In another particular aspect, the disclosure provides a method of identifying the female parental line of melon variety NUN 16108 MEM by analyzing the seed coat of a seed of that variety. In another aspect, the skilled person can determine whether a seed is grown on melon variety NUN 16108 MEM, by analyzing the seed coat or another maternal tissue of said seed.

By crossing and/or selfing (one or more) single traits may be introduced into melon variety NUN 16108 MEM (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g., dominant or recessive) and one or more QTLs (quantitative trait loci) may be transferred into melon variety NUN 16108 MEM by breeding with said variety.

Any pest or disease resistance genes may be introduced into melon variety NUN 16108 MEM, progeny of said variety or into a plant comprising all but 1, 2, or 3 or more of the morphological and physiological characteristics of melon variety NUN 16108 MEM (e.g., as listed in Tables 1 and 2). Resistance to one or more of the following diseases or pests may be introduced into plants described herein: Bacterial Wilt, Root Rot, Crown Blight, Melon Rust, *Podosphaera xanthii* (*Sphaerotheca fuliginea*) race 1, *Podosphaera xanthii* (*Sphaerotheca fuliginea*) race 2, *Podosphaera xanthii* (*Sphaerotheca fuliginea*) race 3, *Podosphaera xanthii* (*Sphaerotheca fuliginea*) race 5, *Golovinomyces cichoracearum* (*Erysiphe cichoracearum*) race 1, *Verticillum* Wilt, Sulphur Burn, Scab, Downy Mildew, *Fusarium oxysporum* f.sp. *melonis* race 0, *Fusarium oxysporum* f.sp. *melonis* race 1, *Fusarium oxysporum* f.sp. *melonis* race 2, *Fusarium oxysporum* f.sp. *melonis* race 1-2, *Fusarium* Wilt R2, Root Knot (Nematode), Anthracnose, Aphid, Pickle Worm, Darkling Ground Beetle, Banded Cucumber Beetle, Mite, Western Spotted Cucumber Beetle, Melon Leafhopper, Melon Worm, Western Striped Cucumber Beetle and/or Melon Leafminer. Other resistances, against pathogenic viruses (e.g., Melon Necrotic Spot Virus (MNSV) resistance, Cucumber Mosaic Virus (CMV), Zucchini Yellow Mosaic Virus (ZYMV), *Papaya* Ringspot Virus (PRSV), Watermelon Mosaic Virus (WMV), Squash Mosaic Virus (SMV), fungi, bacteria, nematodes, insects, or other pests may also be introduced, or other traits such as Melon Yellowing associated Virus (MYaV) resistance and Whitefly resistance.

The disclosure also provides a method for developing a melon plant in a melon breeding program, using melon variety NUN 16108 MEM, or its parts as a source of plant breeding material. Suitable plant breeding techniques are recurrent selection, backcrossing, pedigree breeding, mass selection, mutation breeding and/or genetic marker enhanced selection. In one aspect, the method comprises crossing melon variety NUN 16108 MEM, or its respective progeny, or a plant comprising all but 1, 2, or 3 or more of the morphological and physiological characteristics of melon variety NUN 16108 MEM (e.g., as listed in Tables 1 and 2), with a different melon plant, and wherein one or more offspring of the crossing are subject to one or more plant breeding techniques: recurrent selection, backcrossing, pedigree breeding, mass selection, mutation breeding and genetic marker enhanced selection (see e.g., Vidavsky and Czosnek, (1998) Phytopathology 88(9): 910-4). For breeding methods in general, see, e.g., Principles of Plant Genetics and Breeding, 2007, George Acquaah, Blackwell Publishing, ISBN-13: 978-1-4051-3646-4.

The disclosure also provides a plant comprising at least a first set of the chromosomes of melon variety NUN 16108 MEM, a sample of seed has been deposited under Accession Number NCIMB 43406, optionally further comprising a single locus conversion. In another aspect, the single locus conversion confers a trait wherein the trait is yield, storage, color, flavor, male sterility, herbicide tolerance, insect resistance, pest resistance, disease resistance, environmental stress tolerance, modified carbohydrate metabolism, modified protein metabolism, or ripening.

In one aspect, a plant of variety NUN 16108 MEM may also be mutated (by e.g., irradiation, chemical mutagenesis, heat treatment, etc.) and mutated seeds or plants may be selected in order to change one or more characteristics of said variety. Methods such as TILLING may be applied to populations in order to identify mutants. Similarly, melon variety NUN 16108 MEM may be transformed and regenerated, whereby one or more chimeric genes are introduced into the variety or into a plant comprising all but 1, 2, 3, or more of the morphological and physiological characteristics (e.g., as listed in Tables 1 and 2). Transformation can be carried out using standard methods, such as *Agrobacterium tumefaciens* mediated transformation or biolistics, followed by selection of the transformed cells and regeneration into plants. A desired trait (e.g., gene(s) conferring pest or disease resistance, or tolerance for protection, etc.) can be introduced into melon variety NUN 16108 MEM, or progeny of said variety, by transforming said variety or progeny of said variety with a transgene that confers the desired trait, wherein the transformed plant retains all or all but one, two or three of the morphological and/or physiological characteristics of melon variety NUN 16108 MEM, or the progeny of said variety, and contains the desired trait. In another aspect, the transformation or mutation confers a trait wherein the trait is yield, storage properties, color, flavor, male sterility, herbicide tolerance, insect resistance, pest resistance, disease resistance, environmental stress tolerance, modified carbohydrate metabolism, modified protein metabolism, ripening, or occurs in the intense gene.

The disclosure also provides a method of producing a melon plant having a desired trait comprising mutating the plant or plant part melon variety NUN 16108 MEM and selecting a plant comprising the desired trait, wherein the mutated plant retains all or all but one, two or three of the morphological and physiological characteristics of melon variety NUN 16108 MEM, optionally as described for each variety in Tables 1 and 2, and contains the desired trait and wherein a representative sample of seed of said variety has been deposited under Accession Number NCIMB 43406. In a further aspect, the desired trait is yield, storage properties, color, size, flavor, male sterility, herbicide tolerance, insect resistance, pest resistance, disease resistance, environmental stress tolerance, modified carbohydrate metabolism, modified protein metabolism, ripening, or occurs in the intense gene.

In one aspect, the disclosure provides a method for inducing mutation in melon variety NUN 16108 MEM, comprising:
a) exposing the seed, plant or plant part or cell of melon variety NUN 16108 MEM, to a mutagenic compound or to radiation, wherein a representative sample of seed of said melon variety has been deposited under Accession Number NCIMB 43406;
b) selecting the seed, plant or plant part or cell of melon variety NUN 16108 MEM, having a mutation; and
c) optionally growing and/or multiplying the seed, plant or plant part or cell of melon variety NUN 16108 MEM, having the mutation.

The disclosure also provides a plant having one, two or three physiological and/or morphological characteristics which are different from those of melon variety NUN 16108 MEM and which otherwise has all the physiological and morphological characteristics of said variety, wherein a representative sample of seed of said melon variety has been deposited under Accession Number NCIMB 43406. In particular, variants are encompassed which differ from melon variety NUN 16108 MEM, in no, one, two or three of the characteristics mentioned in Tables 1 and 2 are encompassed.

A part of the plant of variety NUN 16108 MEM (or of progeny of said variety or of a plant having all physiological and/or morphological characteristics but one, two or three which are different from those of said variety) encompasses any cells, tissues, organs obtainable from the seedlings or plants, such as but not limited to: a melon fruit or a part thereof, a cutting, hypocotyl, cotyledon, seed coat, pollen and the like. Such parts can be stored and/or processed further.

The disclosure also provides a plant comprising at least a first set of the chromosomes of melon variety NUN 16108 MEM, a sample of seed has been deposited under Accession Number NCIMB 43406, optionally further comprising a single locus conversion. In another aspect, the single locus conversion confers yield, storage properties, color, size, flavor, male sterility, herbicide tolerance, insect resistance, pest resistance, disease resistance, environmental stress tolerance, modified carbohydrate metabolism, modified protein metabolism, or ripening.

In one aspect, the disclosure provides a haploid plant and/or a doubled haploid plant of melon variety NUN 16108 MEM, or a plant having all but one, two or three physiological and/or morphological characteristics of melon variety NUN 16108 MEM, or progeny of any of these. Haploid and doubled haploid (DH) plants can, for example, be produced by cell or tissue culture and chromosome doubling agents and regeneration into a whole plant. DH production chromosome doubling may be induced using known methods, such as colchicine treatment or the like. In one aspect, the method comprises inducing a cell or tissue culture with a chromosome doubling agent and regenerating the cells or tissues into a whole plant.

In another aspect, the disclosure comprises a method for making doubled haploid cells from haploid cells of melon variety NUN 16108 MEM, comprising doubling cells of said variety with a chromosome doubling agent such as colchicine treatment (see, e.g., Nikolova and Niemirowicz-Szczytt (1996) Acta Soc Bot Pol 65:311-317).

In another aspect, the disclosure provides for haploid plants and/or doubled haploid plants derived from melon variety NUN 16108 MEM that, when combined, make a set of parents of melon variety NUN 16108 MEM. The haploid plant and/or the doubled haploid plant of variety NUN 16108 MEM can be used in a method for generating parental lines of melon variety NUN 16108 MEM.

Using methods known in the art such as "reverse synthesis of breeding lines" or "reverse breeding", it is possible to produce parental lines for a hybrid plant such as melon variety NUN 16108 MEM. A skilled person can take any individual heterozygous plant (called a "phenotypically superior plant" in Example 2 of US2015/0245570 hereby incorporated by reference in its entirety; melon variety NUN 16108 MEM is such plant) and generate a combination of parental lines (reverse breeding parental lines) that, when crossed, produce the variety NUN 16108 MEM. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from US2015/0245570 or from Wijnker et al., Nature Protocols Volume: 9, Pages: 761-772 (2014) DOI: doi:10.1038/nprot.2014.049. Thus, the disclosure provides a method for producing parental lines for a hybrid organism (e.g., melon variety NUN 16108 MEM), comprising in one aspect: a) defining a set of genetic markers present in a heterozygous form (H) in a partially heterozygous starting organism; b) producing doubled haploid lines from spores of the starting organism; c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for the hybrid organism.

In another aspect, the method for producing parental lines for hybrid organisms, e.g., of melon variety NUN 16108 MEM, which when crossed reconstitute the genome of melon variety NUN 16108 MEM, comprising:
  a) defining a set genetic markers that are present a heterozygous form (H) in a partially heterozygous starting organism;
  b) producing at least one further generation from the starting organism by self-pollination (e.g., F2 or F3 generation);
  c) selecting at least one pair of progeny organisms in which at least one genetic marker from the set is present in a complementary homozygous forms (B vs. A, or A vs. B); and
  d) optionally repeating steps b) and c) until at least one pair of progeny organisms that have complementary alleles for at least a subset of the genetic markers has been selected as parental lines for a hybrid.

The disclosure relates to a method of producing a combination of parental lines of a plant of variety NUN 16108 MEM, comprising making doubled haploid cells from haploid cells from said plant or a seed of that plant; and optionally crossing these parental lines to produce and collecting seeds. In another aspect, the disclosure relates to a combination of parental lines produced by this method. In still another aspect, the combination of parental lines can be used to produce a seed or plant of variety NUN 16108 MEM, when these parental lines are crossed. In still another aspect, the disclosure relates to a combination of parental lines from which a seed or plant having all physiological and/or morphological characteristics of melon variety NUN 16108 MEM, (when the characteristics are determined at the 5% significance level for plants grown under the same conditions).

In another aspect, the disclosure provides a method of introducing a single locus conversion or single trait conversion or a desired trait into melon variety NUN 16108 MEM, comprising:
  a) obtaining a combination of a parental lines of melon variety NUN 16108 MEM, optionally through reverse synthesis of breeding lines,
  b) introducing a single locus conversion in at least one of the parents of step a; and
  c) crossing the converted parent with the other parent of step a to obtain seed of melon variety NUN 16108 MEM.

A combination of a male and a female parental line of NUN 16108 MEM can be generated by methods described herein, for example, through reverse synthesis of breeding lines.

In another aspect, the disclosure provides a method of introducing a single locus conversion or single trait conversion or a desired trait into melon variety NUN 16108 MEM, comprising introducing a single locus conversion in at least one of the parents of melon variety NUN 16108 MEM, and crossing the converted parent with the other parent of melon variety NUN 16108 MEM, to obtain seed of said variety.

In another aspect, introducing a single locus conversion in at least one of the parent plants comprises:
  a) obtaining a cell or tissue culture of cells of the parental line of melon variety NUN 16108 MEM;
  b) genetically transforming or mutating said cells;
  c) growing the cells into a plant; and d) optionally selecting plants that contain the single locus conversion, the single trait conversion or the desired trait.

In another method, the step of introducing a single locus conversion in at least one of the parents comprises genetically transforming or mutating cells the parental line of melon variety NUN 16108 MEM, growing the cells into a plant; and optionally selecting plants that contain the single locus conversion, the single trait conversion or the desired trait.

In another embodiment, the step of introducing a single locus conversion, single trait conversion or desired trait in at least one of the parent plants comprises:
- a) crossing the parental line of melon variety NUN 16108 MEM, with a second melon plant comprising the single locus conversion, the single trait conversion or the desired trait;
- b) selecting F1 progeny plants that contain the single locus conversion, the single trait conversion or the desired trait;
- c) crossing said selected progeny plants of step b) with the parental line of step a), to produce a backcross progeny plant;
- d) selecting backcross progeny plants comprising the single locus conversion, the single trait conversion or the desired trait and otherwise all or all but one, two or three of the morphological and physiological characteristics the parental line of step a) to produce selected backcross progeny plants; and
- e) optionally repeating steps c) and d) one or more times in succession to produce selected second, third or fourth or higher backcross progeny plants comprising the single locus conversion, the single trait conversion or the desired trait and otherwise all or all but one, two or three of the morphological and physiological characteristics the parental line of step a) to produce selected backcross progeny plants, when grown in the same environmental conditions.

The disclosure further relates to plants obtained by this method.

In any of the above methods, where the single locus conversion concerns a trait, the trait may be yield or pest resistance or disease resistance. In one aspect, the trait is disease resistance and the resistance is conferred to Bacterial Wilt, Root Rot, Crown Blight, Melon Rust, *Podosphaera xanthii* (*Sphaerotheca fuliginea*) race 1, *Podosphaera xanthii* (*Sphaerotheca fuliginea*) race 2, *Podosphaera xanthii* (*Sphaerotheca fuliginea*) race 3, *Podosphaera xanthii* (*Sphaerotheca fuliginea*) race 5, *Golovinomyces cichoracearum* (*Erysiphe cichoracearum*) race 1, Verticillum Wilt, Sulphur Burn, Scab, Downy Mildew, *Fusarium oxysporum* f.sp. *melonis* race 0, *Fusarium oxysporum* f.sp. *melonis* race 1, *Fusarium oxysporum* f.sp. *melonis* race 2, *Fusarium oxysporum* f.sp. *melonis* race 1-2, *Fusarium* Wilt R2, Root Knot (Nematode), Anthracnose, Aphid, Pickle Worm, Darkling Ground Beetle, Banded Cucumber Beetle, Mite, Western Spotted Cucumber Beetle, Melon Leafhopper, Melon Worm, Western Striped Cucumber Beetle and/or Melon Leafminer. Other resistances, against pathogenic viruses (e.g., Melon Necrotic Spot Virus (MNSV) resistance, Cucumber Mosaic Virus (CMV), Zucchini Yellow Mosaic Virus (ZYMV), *Papaya* Ringspot Virus (PRSV), Watermelon Mosaic Virus (WMV), Squash Mosaic Virus (SMV), fungi, bacteria, nematodes, insects, or other pests may also be introduced, or other traits such as Melon Yellowing associated Virus (MYaV) resistance and Whitefly resistance.

The disclosure also provides a combination of parental lines which, when crossed, produce a seed or plant having all physiological and/or morphological characteristics of melon variety NUN 16108 MEM, but one, two or three characteristics which are different (when grown under the same environmental conditions), as well as a seed or plant having all physiological and/or morphological characteristics of melon variety NUN 16108 MEM, but one, two or three characteristics which are different (when the characteristics are determined at the 5% significance level for plants grown under the same conditions).

In another aspect, the disclosure provides a method of determining the genotype of a plant described herein comprising detecting in the genome (e.g., a sample of nucleic acids) of the plant at least a first polymorphism or an allele. The skilled person is familiar with many suitable methods of genotyping, detecting a polymorphism or detecting an allele including SNP (Single Nucleotide Polymorphism) genotyping, restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium.

The disclosure further provides for food or feed products comprising a part of the plant of variety NUN 16108 MEM, or a part of progeny of said variety, or a part of a plant having all but one, two or three physiological and/or morphological characteristics of melon variety NUN 16108 MEM, comprising one or more of such parts, optionally processed (e.g., canned, chopped, cooked, roasted, in a sauce, in a sandwich, pasted, puréed or concentrated, juiced, frozen, dried, pickled, or powdered).

Melons may also be grown for use as rootstocks (stocks) or scions. Typically, different types of melons are grafted to enhance disease resistance, which is usually conferred by the rootstock, while retaining the horticultural qualities usually conferred by the scion. It is not uncommon for grafting to occur between cultivated melon varieties and related melon species. Methods of grafting and vegetative propagation are well-known in the art.

In another aspect, the disclosure provides to a plant comprising a rootstock or scion of melon variety NUN 16108 MEM.

All documents (e.g., patent publications) are herein incorporated by reference in their entirety, including the following cited references:

UPOV, Guidelines for the Conduct of Tests for Distinctness, Uniformity and Stability, TG104/5, world-wide web at upov.int/edocs/tgdocs/en/tg104.pdf.

US Department of Agriculture, Objective Description of Variety—Muskmelon/Cantaloupe (*Cucumis melo* L.)", world-wide web at ams.usda.gov/ under services/plant-variety-protection/pvpo-c-forms under muskmelon.

Acquaah, Principles of Plant Genetics and Breeding, 2007, Blackwell Publishing, ISBN-13: 978-1-4051-3646-4

Colijn-Hooymans, J. C., et. al., "Competence for Regeneration of Cucumber Cotyledons is Restricted to Specific Developmental Stages", Plant Cell, Tissue and Organ Culture, 1994, vol. 39, pp. 211-217.

Needleman, S. B., et. al., "A General Method Applicable to the Search for Similarities in the Amino Acid Sequence of Two Proteins", Journal of Molecular Biology, 1970, vol. 48(3), pp. 443-53.

Nikolova, V., et. al., "Diploidization of Cucumber (*Cucumis sativus* L.) Haploids by Colchini Treatment", Acta Societas Botanicorum Poloniae, 1996, vol. 65, pp. 311-317.

Parvathaneni, R. K., et al., "Fingerprinting in Cucumber and Melon (*Cucumis* spp.) genotypes Using Morphological and ISSR Markers", Journal of Crop Science and Biotechnology, 2011, vol. 14, no. 1, pp. 39-43. DOI No. 10.1007/s12892-010-0080-1.

Rice, P., et al., "EMBOSS: The European Molecular Biology Open Software Suite", Trends in Genetics, 2000, vol. 16, Issue 6. pp. 276-277.

Ren, Y., et al., "Shoot Regeneration and Ploidy Variation in Tissue Culture of Honeydew Melon (*Cucumis melo* L. inodorus)", In Vitro Cellular & Development Biology-Plant, 2013, vol. 49, p. 223-229.

Vidaysky, F., et. al., "Tomato Breeding Lines Resistant and Tolerant to Tomato Yellow Leaf Curl Virus Issued from *Lycopersicum hirsutum*", The American Phytopathology Society, 1998, vol. 88, no. 9, pp. 910-914.

Vos, P., et al., AFLP: A New Technique for DNA Fingerprinting 1995, Nucleic Acids Research, 1995, vol. 23, No. 21, pp. 4407-4414.

Wijnker, E., et al., Hybrid Recreation by Reverse breeding in *Arabidopsis thaliana*, Nature Protocols, 2014, vol. 9, pp. 761-772. DOI: doi: 10.1038/nprot.2014.049

US2015/0126380
US2015/0245570
US2017/0071145
US2017/0240913
US2017/0335339
https://anrcatalog.ucanr.edu/pdf/7209.pdf
https://anrcatalog.ucanr.edu/pdf/7218.pdf
https://www.ams.usda.gov/resources/st470-muskmelon
http://www.upov.int/edocs/tgdocs/de/tg104.pdf Development of Melon Variety NUN 16108 MEM The hybrid variety NUN 16108 MEM was developed from a male and female proprietary inbred line of Nunhems. The female and male parents were crossed to produce hybrid (F1) seeds of melon variety NUN 16108 MEM. The seeds of melon variety NUN 16108 MEM can be grown to produce hybrid plants and parts thereof (e.g., melon fruit). The hybrid variety NUN 16108 MEM can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the respective female and male parents the Applicant has concluded that melon variety NUN 16108 MEM is uniform and stable.

Deposit Information

A total of 2500 seeds of the hybrid variety NUN 16108 MEM has been deposited according to the Budapest Treaty by Nunhems B.V. on Apr. 25, 2019, at the NCIMB Ltd., Ferguson Building, Craibstone Estate, Bucksburn, Aberdeen AB21 9YA, United Kingdom (NCIMB). The deposit has been assigned NCIMB number 43406. A deposit of melon variety NUN 16108 MEM and of the male and female parent line is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer and will be replaced if it ever becomes nonviable during that period. Applicant does not waive any rights granted under this patent on this application or under the Plant Variety Protection Act (7 U.S.C. § 2321 et seq).

Characteristics of Melon Variety NUN 16108 MEM

The most similar variety to NUN 16108 MEM refers to variety NUN 26191 MEM, a variety from Nunhems B.V., with commercial name Sense 191.

In Tables 1 and 2, a comparison between melon variety NUN 16108 MEM and the Reference Variety are shown based on a trial in the USA. Trial location: Acampo, Calif., USA; Seeding date: Jun. 13, 2019; Harvesting date: Sep. 5, 2019. In Table 3, the distinguishing characteristics between melon variety NUN 16108 MEM and the Reference Variety are shown.

One replication of 30 plants per variety, from which at least 15 plants or plant parts were randomly selected and were used to measure characteristics. For numerical characteristics, averages were calculated. For non-numerical characteristics, the type/degree were determined.

In one aspect, the disclosure provides a plant having the physiological and morphological characteristics of melon variety NUN 16108 MEM as presented in Tables 1 and 2.

TABLE 1

Objective description of melon variety NUN 16108 MEM and the Reference Variety (USDA Descriptors)

| Characteristics | NUN 16108 MEM | NUN 26191 MEM |
| --- | --- | --- |
| Type:<br>1 = Persian; 2 = Honey Dew;<br>3 = Casaba; 4 = Crenshaw; 5 = Common/Summer; 6 = Other | Golden Cantaloupe Long Shelf Life | Golden Cantaloupe Long Shelf Life |
| Area of best adaptation in USA:<br>1 = Southeast; 2 = Northeast/North Central; 3 = Southwest; 4 = Most Areas; 5 = East coast | Arizona, California | Arizona, California |
| Maturity:<br>Days from seeding to harvest | 90 days | 90 days |
| Plant: | | |
| Fertility:<br>1 = Andromonoecious; 2 = Monoecious; 3 = Gynoecious; 4 = Other | Monoecious | Monoecious |
| Habit:<br>1 = Vine; 2 = Semi-bush; 3 = Bush | Vine | Vine |
| Leaf (mature blade of third leaf): | | |
| Shape:<br>1 = Orbicular; 2 = Ovate;<br>3 = Reniform (Cordate) | Reniform | Reniform |
| Lobes:<br>1 = Not Lobed; 2 = Shallowly Lobed; 3 = Deeply Lobed | Not lobed | Not lobed |
| Color:<br>1 = Light Green (Honey Dew); 2 = Medium Green; 3 = Dark Green (Rio Gold) | Dark green | Dark green |
| Color Chart Code (RHS chart): | RHS 137B | RHS N137B |
| Average Length (mm): | 13.51 mm | 12.81 mm |
| Average Width (mm): | 16.31 mm | 15.37 mm |

TABLE 1-continued

Objective description of melon variety NUN 16108 MEM and the Reference Variety (USDA Descriptors)

| Characteristics | NUN 16108 MEM | NUN 26191 MEM |
|---|---|---|
| Surface:<br>1 = Pubescent; 2 = Glabrous;<br>3 = Scabrous<br>Fruit (at edible maturity): | Scabrous | Scabrous |
| Average Length (cm): | 15.48 cm | 16.21 cm |
| Average Diameter (cm): | 14.34 cm | 13.75 cm |
| Average Weight (gram): | 1,748.80 g | 1,612.67 g |
| Shape:<br>1 = Oblate; 2 = Oval; 3 = Round;<br>4 = Elongate-Cylindrical;<br>5 = Spindle; 6 = Acorn | Oval | Oval |
| Surface:<br>1 = Smooth; 2 = Netted;<br>3 = Corrugated; 4 = Warted | Netted | Netted |
| Blossom Scar:<br>1 = Obscure; 2 = Conspicuous | Conspicuous | Conspicuous |
| Rib Presence:<br>1 = Absent; 2 = Present | Absent | Absent |
| Suture Depth:<br>1 = Shallow (Golden Delight);<br>2 = Medium; 3 = Deep (Hackensack) | Very shallow | Very shallow |
| Suture Surface:<br>1 = Smooth; 2 = Netted | Netted | Netted |
| Shipping Quality:<br>1 = Poor (Home Garden); 2 = Fair (Short Distance Shipping); 3 = Excellent (Long Distance Shipping) | Excellent | Excellent |
| Fruit Abscission:<br>1 = When Ripe; 2 = When Overripe; 3 = Do Not Abscise<br>Rind Net: | When overripe | When overripe |
| Net Presence:<br>1 = Absent; 2 = Sparse;<br>3 = Abundant | Sparse | Sparse |
| Distribution:<br>1 = Spotty; 2 = Covers Entire Fruit | Covers entire fruit | Covers entire fruit |
| Coarseness:<br>1 = Fine; 2 = Medium Coarse;<br>3 = Very Coarse | Medium | Medium |
| Interlacing:<br>1 = None;<br>2 = Some; 3 = Complete | Complete | Complete |
| Interstices:<br>1 = Shallow; 2 = Medium Deep;<br>3 = Deep<br>Rind Texture: | Medium deep | Medium deep |
| Texture:<br>1 = Soft; 2 = Firm; 3 = Hard | Soft | Soft |
| Average Thickness at Medial (mm)<br>Rind Color: | 44.38 mm | 42.14 mm |
| 01 - White; 02 = Cream; 03 = Buff;<br>05 = Gold; 06 = Green;<br>08 = Bronze; 09 = Brown;<br>10 = Gray; 11 = Black; 12 = Other<br>Rind Color at Edible Maturity: | | |
| Primary Color (Color Chart Value) | Yellow RHS 153B | Yellow RHS 153C |
| Net Color (Color Chart Value) | White RHS NN155B | Yellowish white RHS NN155A |
| Flesh (at edible maturity) | | |
| Color Near Cavity (Color Chart Value) | Red RHS 173C | Red RHS 173B |
| Color in Center (Color Chart Value) | Red RHS N172B | Red RHS N172A |
| Color Near Rind (Color Chart Value) | Red RHS N172B | Red RHS N172A |
| Refractometer % Soluble Solids (Center of Flesh) | 16.57% | 16.89% |
| Aroma:<br>1 = Absent; 2 = Faint; 3 = Strong | Absent | Absent |
| Flavor:<br>1 = Mild; 2 = Somewhat Spicy;<br>3 = Very Spicy<br>Seed Cavity: | Mild | Mild |
| Length (mm): | 102.58 mm | 108.13 mm |
| Width (mm): | 53.57 mm | 58.32 mm |
| Shape in X-Section:<br>1 = Circular; 2 = Triangular<br>Seeds: | Circular | Circular |
| No. of seeds per fruit | 1,198 | 927 |

TABLE 2

Objective description of melon variety NUN 16108 MEM and the Reference Variety (Non-USDA Descriptors)

| Characteristics | NUN 16108 MEM | NUN 26191 MEM |
|---|---|---|
| Leaf (mature blade of third leaf): | | |
| Development of lobes:<br>Weak, Medium, Strong | Weak to medium | Weak to medium |
| Length of terminal lobe:<br>Short, Medium, Long | Short to medium | Short to medium |
| Dentation of margin:<br>Very weak to Weak, Medium, Strong | Very weak to weak | Very weak to weak |
| Blistering:<br>Weak, Medium, Strong | Weak to medium | Weak to medium |
| Size:<br>Small, Medium, Large | Medium | Medium |
| Petiole attitude:<br>Erect, Semi-erect, Horizontal | Semi-erect | Semi-erect |
| Petiole length, cm: | 100.15 cm | 110.25 cm |
| Petiole width, mm: | 5.81 mm | 6.47 mm |
| Young fruit (unripe fruit, before the color change): | | |
| Hue of green color of skin:<br>Whitish green, Yellowish green, Green, Greyish green | Yellowish green | Yellowish green |
| Length of peduncle, mm: | 46.95 mm | 41.29 mm |
| Thickness of peduncle, mm: | 10.76 mm | 11.32 mm |
| Extension of darker area around peduncle:<br>Absent or very small, Small, Medium, Large<br>Fruit (at edible maturity): | Absent or very small | Absent or very small |
| Change of skin color from young fruit to maturity:<br>Early in fruit development, Late in fruit development, Very late in fruit development | Late in fruit development | Late in fruit development |
| Position of maximum diameter:<br>Toward stem end, at middle, toward blossom end | At middle | At middle |
| Shape in longitudinal section:<br>Ovate, Medium elliptic, Broad elliptic, Circular, Quadrangular, Oblate, Obovate, Elongated | Broad elliptic | Broad elliptic |
| Shape of base:<br>Pointed, rounded, truncate | Rounded | Rounded |
| Shape of apex:<br>Pointed, rounded, truncate | Rounded | Rounded |

TABLE 2-continued

Objective description of melon variety NUN 16108 MEM and the Reference Variety (Non-USDA Descriptors)

| Characteristics | NUN 16108 MEM | NUN 26191 MEM |
|---|---|---|
| Blossom scar diameter, mm: | 15.24 mm | 20.61 mm |
| Size of pistil scar: Small, medium, large | Small to medium | Medium |
| Grooves: Absent or weakly expressed, weakly expressed, strongly expressed | Absent or weakly expressed | Absent or weakly expressed |
| Width of grooves: Narrow, Medium, Broad | Narrow | Narrow |
| Color of grooves: White, Yellow, Green | Yellow | Yellow |
| Creasing of surface: Absent or very weak, weak, medium, strong, very strong | Absent or very weak | Absent or very weak |
| Cork formation: Absent, present | Present | Present |
| Thickness of cork layer: Very thin, thin, medium, thick, very thick | Medium to thick | Medium to thick |
| Pattern of cork formation: Dots only, dots and linear, linear only, linear and netted, netted only | Netted only | Netted only |
| Density of pattern of cork formation: | Dense | Dense |
| Rind color: | | |
| Ground color of skin: White, yellow, green, gray | Yellow | Yellow |
| Intensity of ground color of skin: Light, medium, dark | Light to medium | Light to medium |
| Density of dots: Absent or very sparse, sparse, medium, dense, very dense | Absent or very sparse | Absent or very sparse |
| Density of patches: Absent or very sparse, sparse, medium, dense, very dense | Very small | Very small |
| Warts: Absent, present | Absent | Absent |
| Flesh (at edible maturity): | | |
| Penetrometer, kg: | 3.94 kg | 2.73 kg |
| Firmness: Soft, Medium, Firm | Soft | Firm |
| Seeds: | | |
| Seed shape: Not pine-nut shape, pine-nut shape | Not pine nut | Not pine nut |
| Seed color: Whitish, creamy yellow | Creamy yellow | Creamy yellow |
| Maturity: | | |
| Time of male flowering: Early, Medium, Late | Medium | Medium |
| Time of female flowering: Early, Medium, Late | Medium | Medium |
| Time of ripening: Very early, Early, Medium, Late, Very late | Late | Late |

TABLE 3

Distinguishing Characteristics between melon variety NUN 16108 MEM and the Reference Variety

| Characteristics | NUN 16108 MEM | NUN 26191 MEM |
|---|---|---|
| Leaf (mature blade of third leaf): | | |
| Average Length (mm): | 13.51 mm | 12.81 mm |
| Average Width (mm): | 16.31 mm | 15.37 mm |
| Petiole length, cm: | 100.15 cm | 110.25 cm |
| Petiole width, mm: | 5.81 mm | 6.47 mm |
| Young fruit (unripe fruit, before the color change): | | |
| Length of peduncle, mm: | 46.95 mm | 41.29 mm |
| Fruit (at edible maturity): | | |
| Average Length (cm): | 15.48 cm | 16.21 cm |
| Average Diameter (cm): | 14.34 cm | 13.75 cm |
| Average Weight (gram): | 1,748.80 g | 1,612.67 g |
| Blossom scar diameter, mm: | 15.24 mm | 20.61 mm |
| Average Thickness at Medial (mm) | 44.38 mm | 42.14 mm |
| Size of pistil scar: Small, medium, large | Small to medium | Medium |
| Rind color: | | |
| Primary Color | Yellow | Yellow |
| (Color Chart Value) | RHS 153B | RHS 153C |
| Net Color | White | Yellowish white |
| (Color Chart Value) | RHS NN155B | RHS NN155A |
| Flesh (at edible maturity): | | |
| Color Near Cavity | Red | Red |
| (Color Chart Value) | RHS 173C | RHS 173B |
| Color in Center | Red | Red |
| (Color Chart Value) | RHS N172B | RHS N172A |
| Color Near Rind | Red | Red |
| (Color Chart Value) | RHS N172B | RHS N172A |
| Penetrometer kg: | 3.94 kg | 2.73 kg |
| Seed Cavity: | | |
| Length (mm): | 102.58 mm | 108.13 mm |
| Width (mm): | 53.57 mm | 58.32 mm |
| Seeds: | | |
| No. of seeds per fruit | 1.198 | 927 |

The invention claimed is:

1. A plant, plant part or seed of melon variety NUN 16108 MEM, wherein a representative sample of seed of said melon variety has been deposited under Accession Number NCIMB 43406.

2. The plant part of claim 1, wherein said plant part is a leaf, pollen, an ovule, a cell, a fruit, a scion, a root, a rootstock, a cutting, or a flower.

3. A seed that produces the plant of claim 1.

4. A seed grown on the plant of claim 1, wherein the plant grown from said seed does not differ from the plant of claim 1 when the characteristics are determined at the 5% significance level when grown under the same environmental conditions.

5. A melon plant having all of the physiological and morphological characteristics of the plant of claim 1.

6. A melon plant or a part thereof derived from the plant of claim 1 which does not differ from the plant of claim 1 in any of the characteristics of melon variety NUN 16108 MEM, when the characteristics are determined at the 5% significance level when grown under the same environmental conditions, wherein a representative sample of seed of melon variety NUN 16108 MEM has been deposited under Accession Number NCIMB 43406.

7. A tissue or cell culture comprising regenerable cells of the plant of claim 1.

8. The tissue or cell culture according to claim 7, comprising cells or protoplasts from a plant part suitable for vegetative reproduction, wherein the plant part is an embryo, a meristem, a fruit, a leaf, pollen, an ovule, a cell, a petiole, a shoot, a stem, a root, a root tip, a cutting, a hypocotyl, a cotyledon, a scion, a stock, a rootstock, a pistil, an anther, a flower, a seed, a stem, or a stalk.

9. A melon plant regenerated from the tissue or cell culture of claim 7, wherein the plant has all of the physiological and morphological characteristics of the plant of variety NUN 16108 MEM, when the characteristics are determined at the 5% significance level for plants grown under the same environmental conditions, and wherein a representative sample of seed of said melon variety has been deposited under Accession Number NCIMB 43406.

10. A method of producing the plant claim 1 or a part thereof, said method comprising vegetative propagation of at least a part of the plant of melon variety NUN 16108 MEM, wherein a representative sample of seed of said melon variety has been deposited under Accession Number NCIMB 43406.

11. The method of claim 10, wherein said vegetative propagation comprises regenerating a whole plant from said part of the plant of melon variety NUN 16108 MEM, wherein a representative sample of seed of said melon variety has been deposited under Accession Number NCIMB 43406.

12. The method of claim 10, wherein said part is a cutting, a cell culture, or a tissue culture.

13. A vegetative propagated plant of claim 1, or a part thereof, wherein the vegetative propagated plant has all of the physiological and morphological characteristics of the plant of melon variety NUN 16108 MEM, when the characteristics are determined at the 5% significance level for plants grown under the same environmental conditions, and wherein a representative sample of seed of said melon variety has been deposited under Accession Number NCIMB 43406.

14. A method of producing a melon plant, said method comprising crossing the plant of claim 1 with a second plant at least once, and selecting a progeny melon plant from said crossing and optionally allowing the progeny melon plant to form seed.

15. A first generation progeny plant of the plant of claim 1, obtained by selfing or cross-pollinating the plant of claim 1 with another melon plant, wherein said progeny plant has all of the physiological and morphological characteristics of the plant of melon variety NUN 16108 MEM, when the characteristics are determined at the 5% significance level for plants grown under the same environmental conditions, and wherein a representative sample of seed of said melon variety has been deposited under Accession Number NCIMB 43406.

16. A melon plant derived from the plant of claim 1 having one physiological or morphological characteristic which is different from the plant of claim 1, and which otherwise has all the physiological and morphological characteristics of the plant of melon variety NUN 16108 MEM, when the characteristics are determined at the 5% significance level for plants grown under the same environmental conditions, wherein a representative sample of seed of said melon variety has been deposited under Accession Number NCIMB 43406.

17. The plant of claim 1, further comprising a single locus conversion, wherein said plant has all of the morphological and physiological characteristics of the plant of melon variety NUN 16108 MEM, when the characteristics are determined at the 5% significance level for plants grown under the same environmental conditions, and wherein a representative sample of seed of said melon variety has been deposited under Accession Number NCIMB 43406, optionally wherein the single locus conversion confers male sterility, herbicide tolerance, insect resistance, pest resistance, disease resistance, environmental stress tolerance, modified carbohydrate metabolism, modified protein metabolism, or ripening.

18. A method of producing doubled haploid cells of the plant of claim 1, said method comprising making double haploid cells from haploid cells from the plant or seed of melon variety NUN 16108 MEM, wherein a representative sample of seed of said melon variety has been deposited under Accession Number NCIMB 43406.

19. A method of grafting the scion or rootstock of the plant of melon variety NUN 16108 MEM, said method comprising attaching tissue from the scion or rootstock of claim 2 to the tissue of a second plant, and optionally regenerating a plant therefrom.

20. A container comprising the plant, plant part or seed of claim 1.

21. A food, or a feed product, or a processed product comprising the plant part of claim 2, wherein the plant part is a fruit or a part thereof.

22. A method of producing a melon plant having a desired trait, said method comprising mutating a plant of melon variety NUN 16108 MEM and selecting a mutated plant with a desired trait, wherein the mutated plant contains the desired trait and retains all of the physiological and morphological characteristics of melon variety NUN 16108 MEM, when the characteristics are determined at the 5% significance level for plants grown under the same environmental conditions, and wherein a representative sample of seed of said melon variety has been deposited under Accession Number NCIMB 43406, and wherein the desired trait is male sterility, herbicide tolerance, insect resistance, pest resistance, disease resistance, environmental stress tolerance, modified carbohydrate metabolism, modified protein metabolism, or ripening.

* * * * *